United States Patent
Hahn et al.

(10) Patent No.: US 8,087,799 B2
(45) Date of Patent: Jan. 3, 2012

(54) ILLUMINATION MEANS AND INSPECTION MEANS HAVING AN ILLUMINATION MEANS

(75) Inventors: Kurt Hahn, Giessen (DE); Michael Hofmann, Heuchelheim (DE); Christof Krampe-Zadler, Castrio-Rauxel (DE)

(73) Assignee: Vistec Semiconductor Systems GmbH, Weilburg (DE)

( * ) Notice: Subject to any disclaimer, the term of this patent is extended or adjusted under 35 U.S.C. 154(b) by 300 days.

(21) Appl. No.: 12/286,253

(22) Filed: Sep. 29, 2008

(65) Prior Publication Data
US 2009/0086483 A1 Apr. 2, 2009

(30) Foreign Application Priority Data
Oct. 2, 2007 (DE) .......... 10 2007 047 352

(51) Int. Cl.
*F21V 1/04* (2006.01)
(52) U.S. Cl. .......... 362/235; 362/249.02; 362/249.06; 362/307; 356/237.1; 356/237.2
(58) Field of Classification Search .......... 362/227–248, 362/249.01–241.19, 307–309; 382/145; 356/237.1–237.4
See application file for complete search history.

(56) References Cited

U.S. PATENT DOCUMENTS

| | | | | |
|---|---|---|---|---|
| 4,893,223 A | * | 1/1990 | Arnold | 362/11 |
| 5,828,449 A | * | 10/1998 | King et al. | 356/237.1 |
| 6,053,621 A | * | 4/2000 | Yoneda | 362/245 |
| 6,139,162 A | * | 10/2000 | Masaki | 362/618 |
| 6,554,452 B1 | * | 4/2003 | Bourn et al. | 362/247 |
| 6,874,911 B2 | * | 4/2005 | Yoneda | 362/294 |
| 7,325,946 B2 | * | 2/2008 | Tyson | 362/260 |
| 7,489,394 B2 | * | 2/2009 | Wienecke et al. | 356/237.2 |
| 2003/0169916 A1 | | 9/2003 | Hayashi et al. | |
| 2003/0184743 A1 | * | 10/2003 | Hiramoto et al. | 356/237.1 |
| 2005/0013474 A1 | | 1/2005 | Sim | |
| 2006/0072105 A1 | * | 4/2006 | Wagner | 356/237.1 |
| 2006/0119366 A1 | | 6/2006 | Iffland et al. | |
| 2007/0188745 A1 | * | 8/2007 | Smedt | 356/237.2 |
| 2007/0258085 A1 | * | 11/2007 | Robbins et al. | 356/237.4 |

FOREIGN PATENT DOCUMENTS

| | | |
|---|---|---|
| DE | 102004058128 A1 | 6/2006 |
| DE | 102005014596 B3 | 1/2007 |
| DE | 102007024525 A1 | 9/2008 |
| EP | 1348947 A1 | 10/2003 |

\* cited by examiner

*Primary Examiner* — Jong-Suk (James) Lee
*Assistant Examiner* — Stanley Weinberg
(74) *Attorney, Agent, or Firm* — Simpson & Simpson, PLLC

(57) ABSTRACT

An illumination mean for the inspection of flat substrates is disclosed. The flat substrate includes an upper edge area, a lower edge area and a front area. The illumination means is formed as an annular segment and comprises an opening into which at least the edge area of the flat substrate extends. A plurality of light sources are arranged on an annular segment in a housing. Inside the housing, a reflective element is provided so that the light from the light sources does not impinge perpendicularly on the upper edge area, the lower edge area and the front area of the flat substrate.

21 Claims, 7 Drawing Sheets

US 8,087,799 B2

ILLUMINATION MEANS AND INSPECTION MEANS HAVING AN ILLUMINATION MEANS

CROSS REFERENCE TO RELATED APPLICATIONS

This patent application claims priority of German Patent Application No. 10 2007 047 352.6, filed on Oct. 2, 2007, the application is incorporated herein by reference.

FIELD OF THE INVENTION

The present invention relates to an illumination means. In particular, the invention relates to an illumination means for the illumination of the edge area of flat substrates. The flat substrate has an upper edge area, a lower edge area and a front area. The illumination means is designed as an annular segment, and the area to be illuminated of the flat substrate extends into the opening of the annular segment.

The invention also relates to an inspection means having an illumination means. The inspection means comprises several work stations and a changer delivering a flat substrate to the various work stations.

BACKGROUND OF THE INVENTION

U.S. Patent Application No. 2005/0013474 discloses a device wherein the edge area of a wafer is also examined or inspected with the help of three cameras. However, the document does not discuss the design of the illumination means for the edge area of the wafer.

U.S. Patent Application No. 2003/0169916 discloses a device using three cameras to acquire images of the front side of the wafer edge and of the two chamfers at the wafer edge, respectively. The cameras are arranged such that the first camera is opposite to the upper chamfer of the wafer edge, that a second camera is opposite to the front side of the wafer edge, and that a third camera is opposite to the lower chamfer of the wafer edge. The patent application does not discuss the design of the illumination means for illuminating the wafer edge.

German Patent application DE 10 2007 024 525.6, which has not been laid open yet, discloses a device and a method for evaluating defects in the edge area of a wafer. In one embodiment, an illumination means is described that is designed as an annular segment. The illumination means is a calotte having a plurality of light sources attached thereto. The calotte is provided with a diffusely transparent screen or a diffuser, which thus contributes to a higher homogeneity of the illumination. The calotte comprises a recess via which the edge of the wafer is captured. The wafer extends into the interior of the calotte. The illumination elements arranged on the calotte may be implemented as LEDs emitting white light. Illumination elements are arranged on the calotte such that a bright field illumination is achieved at the edge of the wafer.

SUMMARY OF THE INVENTION

It is the object of the invention to provide a compact and variable illumination source for the illumination of the edge area of a flat substrate.

This object is achieved by an illumination means comprising: an annular segment defining an opening into which at least an edge area of a wafer extends; a plurality of light sources formed as light-emitting diodes being arranged on the annular segment in a housing on a board; a reflective element is provided inside the housing such that the light from the light sources does not impinge perpendicularly on an upper edge area, a lower edge area and a front area of the wafer, and wherein the plurality of light sources are opposite the reflective element inside the housing.

It is further an object of the invention to provide an inspection means with which the edge area of a wafer may be illuminated variably from all sides.

This object is achieved by an inspection means comprising: at least one work station; a changer for supplying a wafer to the at least one of the work stations; an illumination means associated with at least one of the work stations, wherein the illumination means is formed as an annular segment and surrounds at least an edge area of the wafer; a plurality of light sources are arranged on a board which also has the shape of an annular segment in a housing, a reflective element being provided inside the housing, such that the light from the light sources does not impinge perpendicularly on an upper edge area, a lower edge area and a front area of the wafer, and wherein the plurality of light sources are opposite the reflective element inside the housing.

It is particularly advantageous if a plurality of light sources are arranged on an annular segment in a housing in the illumination means. A reflective element is provided inside the housing such that the light of the light sources does not impinge perpendicularly on the upper edge area, the lower edge area and the front area of the flat substrate.

The light sources located in the housing are implemented as light-emitting diodes. The light-emitting diodes are arranged on a board also designed in the shape of an annular segment. The board with the light-emitting diodes is inserted in the housing such that the light-emitting diodes are opposite to a reflective element inside the housing.

The plurality of light-emitting diodes are evenly distributed on the circular segment-like board. The circular segment-like board may be divided into several segments that may be operated separately. In a preferred embodiment of the invention, each segment of the board contains the same number of light-emitting diodes. The circular segment-like board is mounted on a cooling body for cooling and dissipating waste heat. The dissipation of waste heat is particularly important if the light sources on the board are implemented as high-performance light-emitting diodes.

The housing of the illumination means essentially consists of the board in the shape of a circular segment, a cover of the metallic housing portion opposite the upper edge area, the lower edge area and the front area of the flat substrate or the wafer, and a window for the passage of light from the light sources. At each of the two ends, the housing is closed by a lid. In the following description, the terms flat substrate and wafer are used as synonyms.

A diffusely scattering optical element is provided in the window for the passage of light from the light sources. A diffractive optical element for beam shaping may also be provided in the window for the passage of light from the light sources. In a further embodiment, it is contemplated that a combination of the diffusely scattering optical element and the diffractive optical element for beam shaping is provided in the window.

The diffusely scattering optical element may be a film inserted between the metallic housing portion having the reflective element and the cover of the metallic housing portion.

The reflective element is formed as an integral part of the housing. The reflective element may be provided with such a shape that it may be used for beam shaping for the light from the light sources. The metallic housing portion having the reflective element is made as a rotary part of aluminum and is provided with a correspondingly reflective coating for increased reflectivity. The reflective coating may be a metal coating and/or a dielectric coating. The dielectric coating additionally performs a filtering function for the light from the light sources.

The light from the light sources may be monochromatic. The light from the light sources may also be polychromatic. In a further embodiment of the invention, the light from the light sources may be set to be monochromatic and/or polychromatic. The light sources implemented as LEDs may emit light of different colors. The light sources arranged on the various segments may be designed such that each segment is loaded with different color LEDs.

BRIEF DESCRIPTION OF THE DRAWINGS

In the following, embodiments will explain the invention and its advantages in more detail with reference to the accompanying drawings, in which.

DETAILED DESCRIPTION OF THE INVENTION

Figure 1:
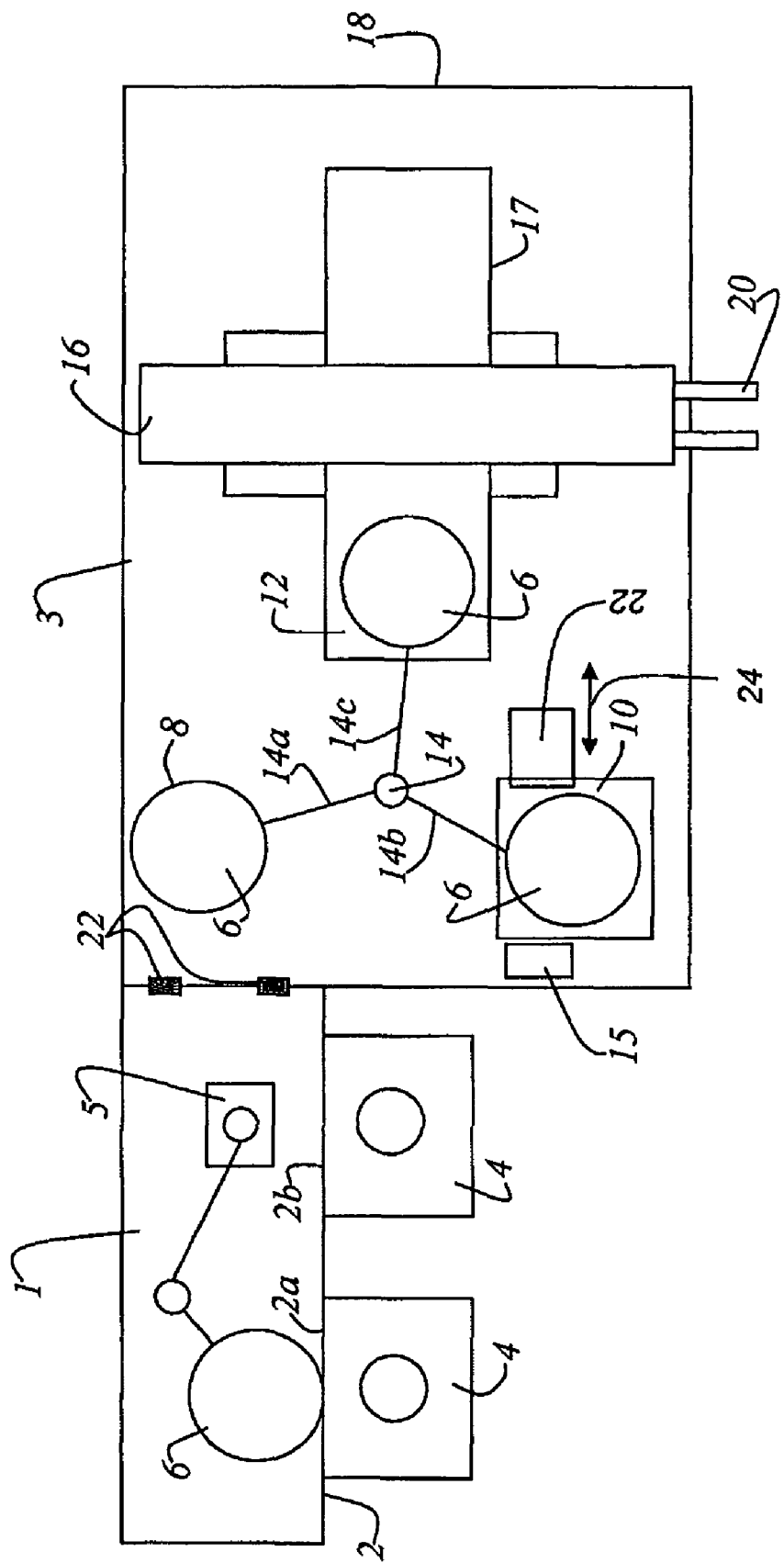
FIG. 1 shows a schematic view of the inner structure of an inspection means for wafers where the present invention may be employed.

FIG. 1 schematically shows the inner structure of a means for inspecting wafers 6, where the inventive illumination means is employed. A substrate supply module 1 is laterally associated with the means 3. The means 3 for wafer inspection includes several work stations 9, 10 and 12. In this embodiment, the substrate supply module 1 is oriented with respect to means 3 such that it may be loaded with substrates at the front 2 via one or more load ports 2a, 2b. Open design or closed cartridges are used for this purpose, which are inserted into the load ports 2a, 2b manually by the user or by automation, for example by means of a robot. The cartridges 4 may be filled with wafers, or they may be empty, depending on the intended work process. For example, all cartridges may be filled, and wafers 6 are first taken from one cartridge, inserted into means 3 and returned to the same cartridge 4 after processing and inspection there.

Predetermined examinations, checks and inspections of the wafer are performed at the work stations 9, 10 and 12. In the present embodiment, three work stations 9, 10 and 12 are provided in means 3. Although the following description relates to wafers, this is not to be considered as limiting the invention. The present invention may, in principle, also be used for flat substrates whose edge areas are to be inspected. A changer 14 distributing the wafer or wafers to the various work stations 9, 10 and 12 is provided in the center between the work stations 9, 10 and 12. The changer 14 has three arms 14a, 14b and 14c. The first work station 9 generally serves for receiving the wafers 6 from the substrate supply module. The wafers 6 may also be returned from the means for wafer inspection to the substrate supply module at the first work station 9.

The second work station 10 serves for orienting, for determining the positioning and/or for visually inspecting the wafers 6. For the orientation of the wafers 6, the second work station 10 has a measuring means associated therewith, which detects the markers applied to the wafer and determines codings of the wafers. The measuring means 15 further determines the deviation from the exact positional deposition of the wafer in the second work station 10. This work station will be referred to as prealigner 10 in the following description. The measuring means 15 allows determining the lateral runout of the wafer 6, which is caused by the imprecise deposition of the wafer on the prealigner 10 by the three-paddle handler 14. The center offset of the wafer is corrected by the prealigner 10. The data thus determined are forwarded to a central processing unit (not shown).

The third work station 12 is designed for micro-inspection of the wafers 6. The third work station comprises an X/Y table 17 supplying the wafer 6 to a microscope 16 for micro-inspection. Z-adjustment may also be allowed by the X/Y table. A device 22 for visually inspecting wafers in the edge area of the wafer 6 is also associated with the second work station 10. As also shown in FIG. 1, the device for visually inspecting the edge area of the wafer 6 may be moved towards the edge area of the wafer 6 or away from the edge 8 of the wafer 6 in the direction of the double arrow 24. The movement of the device 22 is not to be considered as limiting the invention. Someone skilled in the art will understand that the device for visually inspecting the edge area 8 of the wafer is arranged to be stationary with respect to the wafer and/or the work station 10. The movement of the device 22 only serves to allow the deposition of the wafer on the second work station 10 without any obstacles. The description of the inspection means is not to be considered as limiting the invention. It is obvious for someone skilled in the art that the inventive illumination means is also used in a stand-alone device that only inspects the edge of a flat substrate. Neither is the invention limited to the use of a three-paddle handler. Any handler may be used that is suitable to position the flat substrate so that it is in operative connection with the illumination means.

Figure 2:
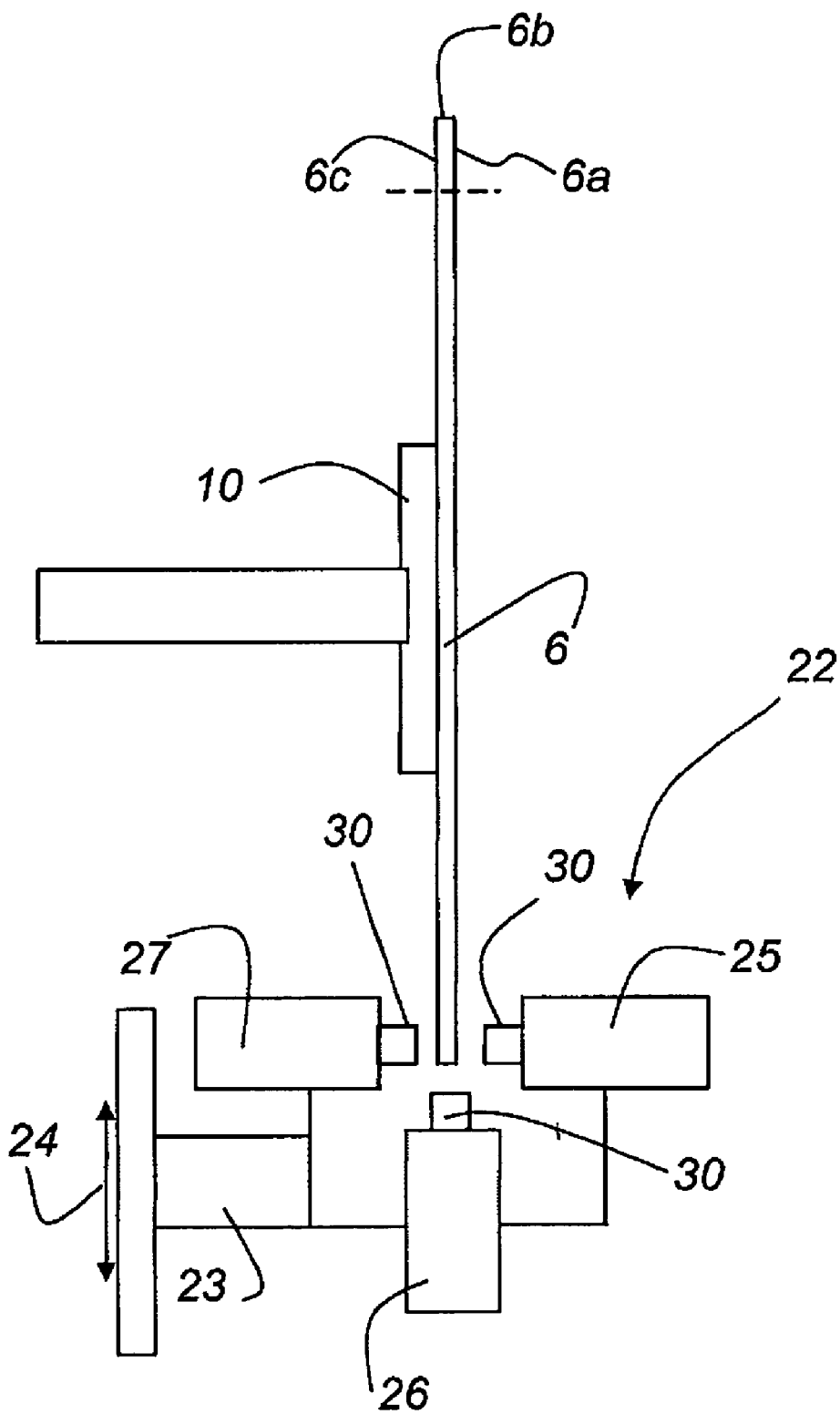
FIG. 2 shows a schematic representation of the arrangement of the device for visually inspecting defects in the edge area of a wafer.

FIG. 2 shows a schematic representation of the device for visually evaluating defects in the edge area of the wafer 6. The wafer 6 is deposited on the prealigner 10. Someone skilled in the art will understand that the wafer is to be seen as a flat substrate. As mentioned in FIG. 1, the prealigner 10 is arranged in a means for inspecting wafers 6. A first camera 25, a second camera 26 and a third camera 27 are arranged on a common carrier 23. In the embodiment shown, the common carrier may be moved in a radial direction with respect to the wafer 6. Each camera 25, 26 and 27 is provided with an objective 30. The direction of movement is indicated by the double arrow 24. The distance covered by the common carrier 23 ranges between 30 and 40 mm. The first camera 25 allows inspecting the upper edge area 6a. The second camera 26 allows inspecting the front 6b of the wafer 6. The third camera 27 allows inspecting or capturing the lower edge area 6c of the wafer 6.

Figure 3:
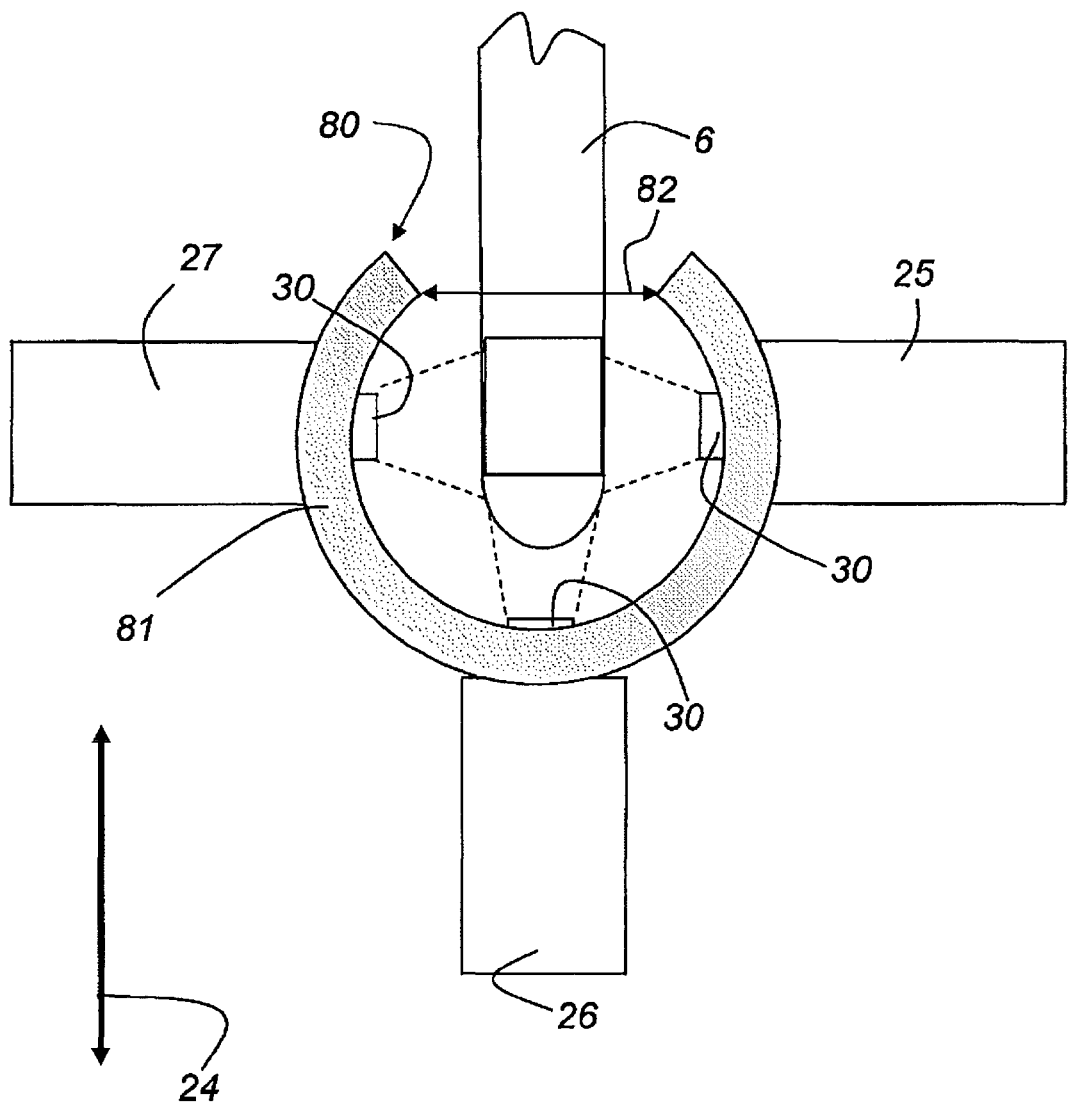
FIG. 3 shows a schematic arrangement of the illumination means in connection with the cameras with respect to the edge area of the wafer.

FIG. 3 schematically shows an embodiment of the arrangement of the cameras 25, 26 and 27 and the inventive illumination means 80. The illumination means 80 is shown as an annular segment 81. Starting from the annular segment 81, the edge area of the wafer is illuminated. The illumination means 80 is provided with a diffusely transparent screen or diffuser (not shown), which thus contributes to a higher homogeneity of the illumination. The cameras 25, 26 and 27 are also arranged near the illumination means 80. These cameras 25, 26 and 27 each serve for capturing a defect in the edge area of the wafer edge. In the capturing position, the cameras 25, 26 and 27 and the required illumination are thus located opposite the lower side, the front and/or the upper side of the wafer. The illumination means 80 comprises an opening 82 to receive the edge of the wafer, which thus extends into the interior of the illumination means 80. As discussed in the following description, the illumination means 80 includes a plurality of light sources.

Figure 4:
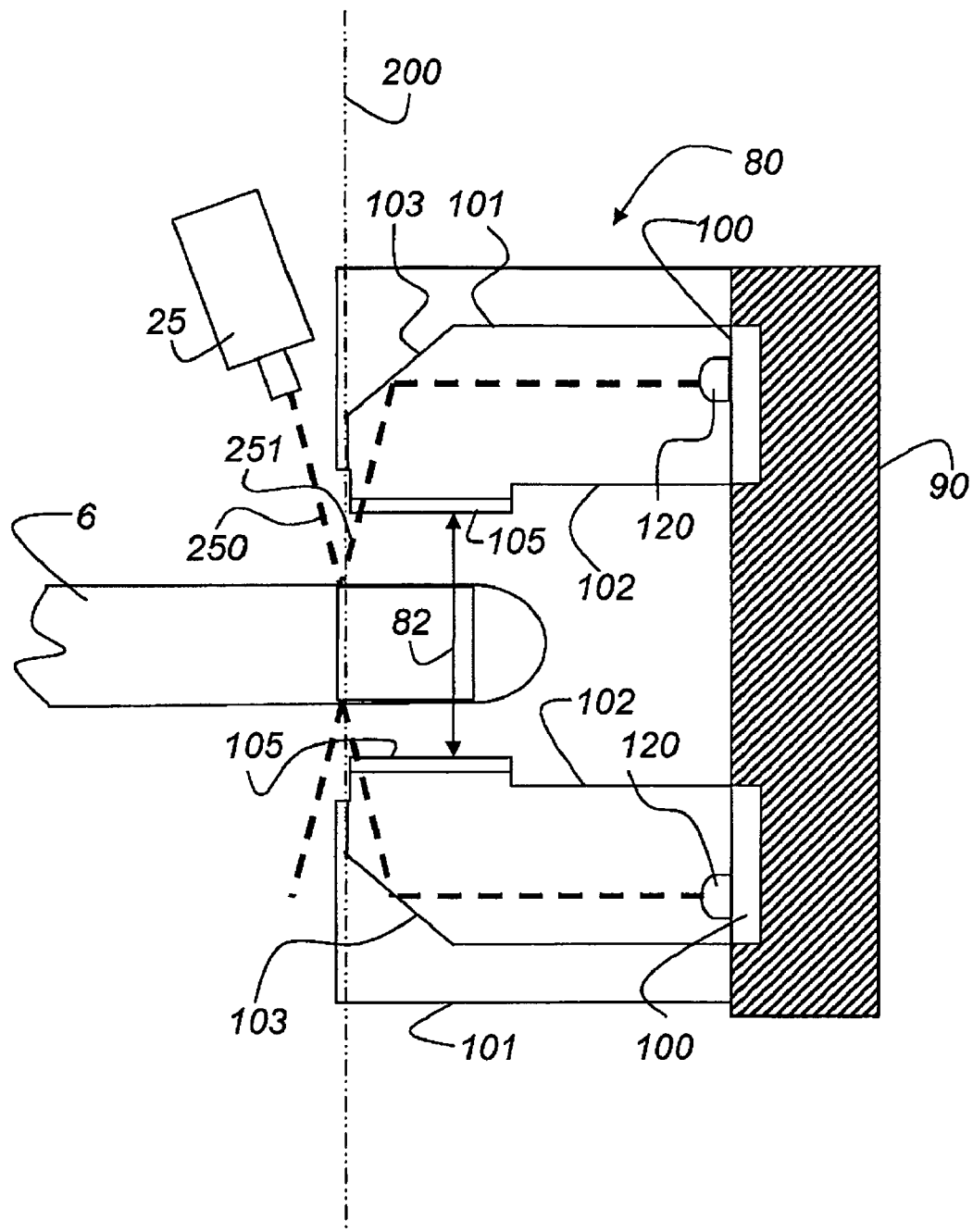
FIG. 4 shows a schematic cross-section of the inventive illumination device.

FIG. 4 schematically shows the spatial association of the wafer 6 with the illumination means 80. The housing of the illumination means 80 essentially consists of the board 100 carrying the light sources 120. The board 100 is connected to a metallic housing portion 101 having a reflective element 103 formed therein. There is further provided a cover 102 forming a self-contained housing together with the board 100 and the metallic housing portion 101. The inventive illumination means 80 is provided with a cooling body 90 connected to the board 100 carrying the light sources 120. The cooling body essentially serves for dissipating the excess heat generated by the light sources. The illumination means 80 is designed as an open annular segment, which thus includes an opening 82 into which the edge area of the wafer 6 extends. The light coming from the light sources 120 of the board reaches the surface of the wafer via the reflective element 103 in the upper housing portion 100 after traveling in a beam path between the light sources 120 and the reflective element 103 is arranged essentially parallel to the upper edge area and the lower edge area of wafer 6 as seen by the bold broken lines in FIG. 4. The light from the light sources thus arrives at an angle with respect to the surface normal 200 of the wafer. The camera 25 is arranged at the same angle as that at which the light from the illumination means 80 impinges on the wafer, so that its optical axis 250 is inclined at the same angle as the light 251 impinging on the surface of the wafer 6. If these two angles are equal, the result is a so-called bright field arrangement. If the two angles are unequal, the result is a so-called dark field arrangement. The light from the light sources 120 reaches the surface of the wafer 6 via a transparent window or a diffusely scattering window 105.

Figure 5:
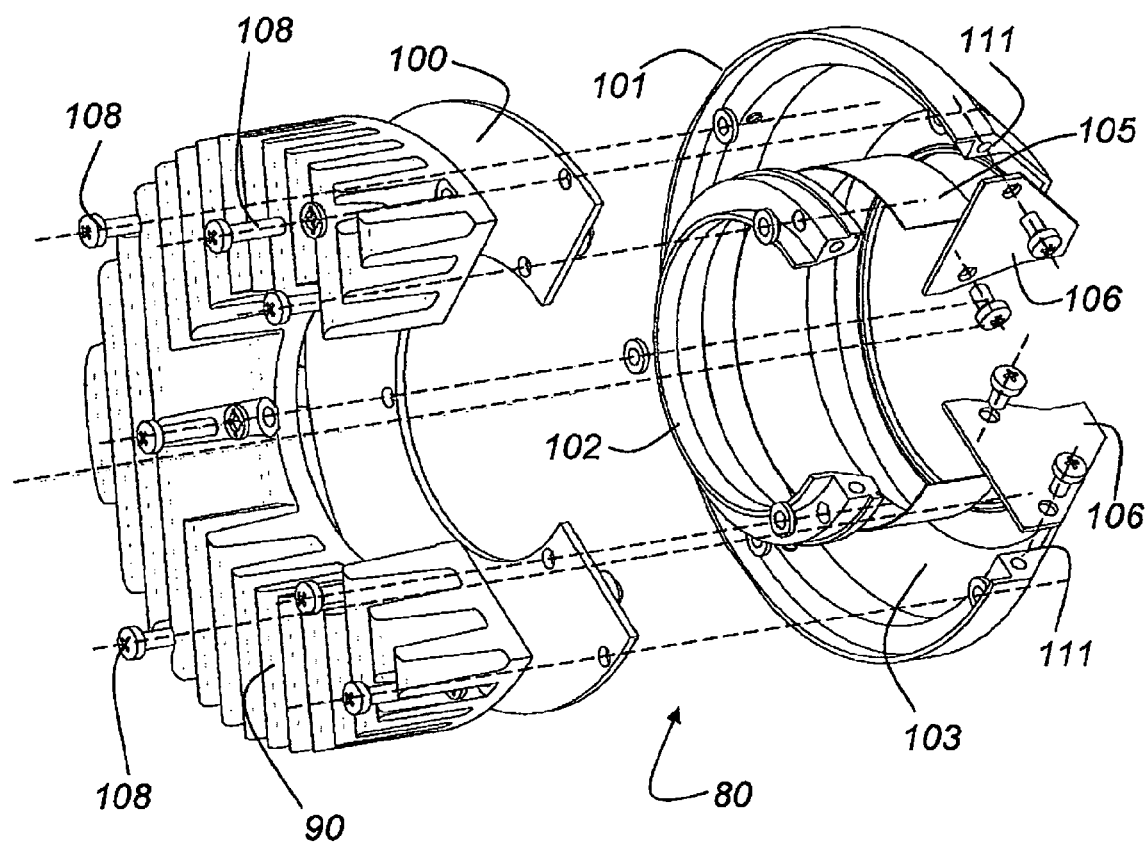
FIG. 5 shows an exploded view of the inventive illumination means.

FIG. 5 shows an exploded view of the inventive illumination means 80. The cooling body 90 is mounted on the board 100 by means of several screws 108. The metallic housing portion 101 including the reflective element 103 is placed on the board 100. A cover 102 is also provided with the board 100, wherein the transparent window 105 is formed between the cover 102 and the metallic housing portion 101. The end areas 111 of the housing of the illumination means 80 are each closed with a lid 106.

Figure 6:
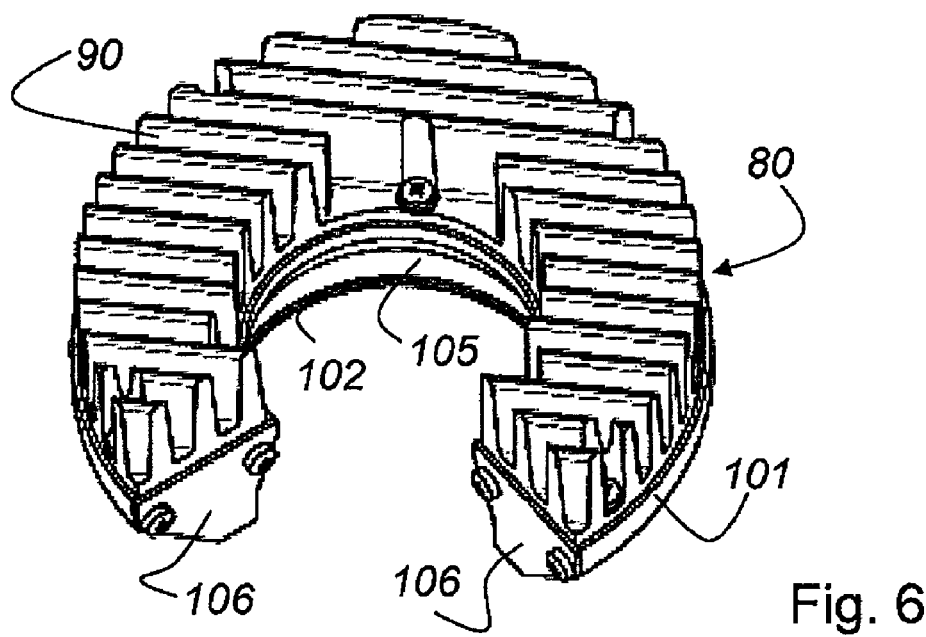
FIG. 6 shows a perspective view of the assembled illumination means showing the rear view of the illumination means.

FIG. 6 shows a perspective view of the illumination means 80 in the assembled state. As already mentioned in the description associated with FIG. 5, the cooling body 90 rests on the metallic housing portion 101 and forms a closed housing together with the board 90, the cover 102 and the lids 106 on the end areas of the illumination means 80.

Figure 7:
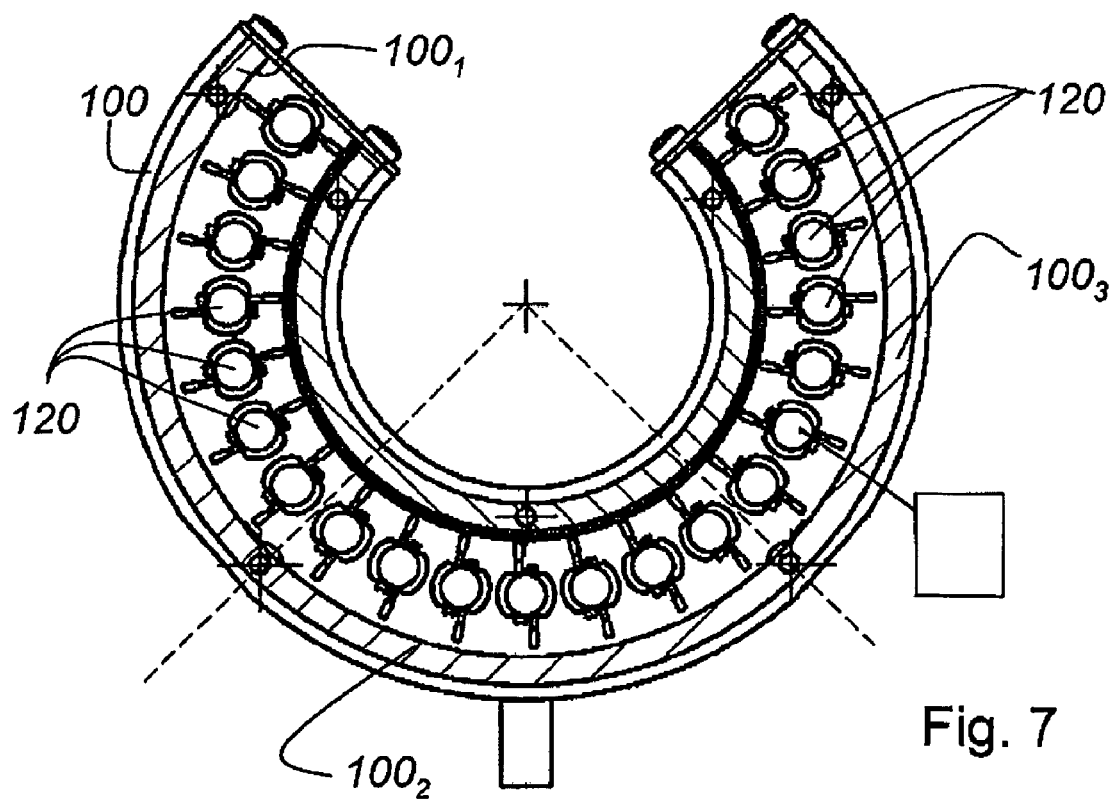
FIG. 7 shows a top view of the board loaded with the light sources.

FIG. 7 shows a top view of the board 100 carrying a plurality of light sources 120. The light sources 120 are formed by LEDs. The light coming from the light sources may, for example, be monochromatic. It is also possible that the light coming from the light sources 120 is polychromatic. It is also contemplated that the light coming from the board 100 is a mixture of polychromatic and monochromatic illumination. In the embodiment of the board 100 shown in FIG. 7, the same is divided into three segments $100_1$, $100_2$ and $100_3$ of equal size. This division is only one of many possible embodiments and is not to be considered as limiting the invention. Someone skilled in the art will understand that the annular segment-like board 100 may be divided into several segments $100_1$, $100_2$ and $100_3$ that may be driven separately. Each of the segments $100_1$, $100_2$ and $100_3$ carries a certain number of light sources 120. In a preferred embodiment, the light sources 120 are implemented as light-emitting diodes. For this reason, it is necessary to mount the board 100 with the light sources 120 on the cooling body 90. By driving the individual segments $100_1$, $100_2$ and $100_3$ separately, it is possible to realize a plurality of illumination conditions on the surface or on the lower side or the frontal area of the wafer 6. The individual segments on the board 100 may thus also be provided with different color LEDs.

Figure 8:
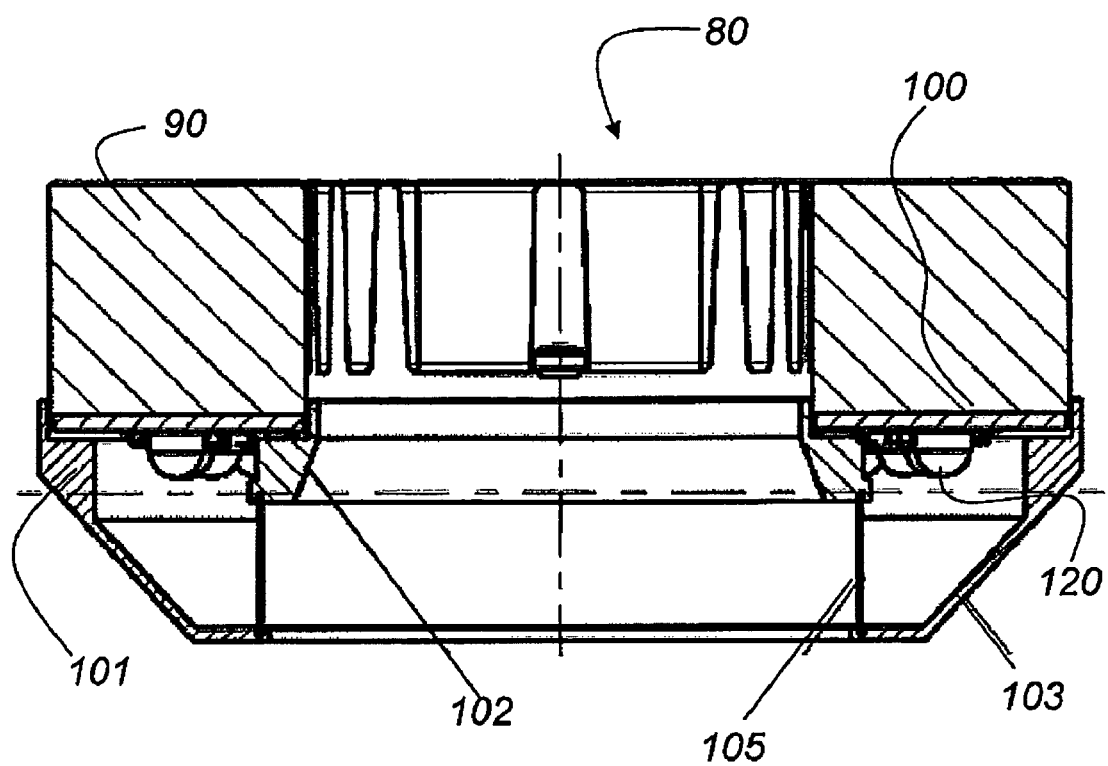
FIG. 8 shows the inventive illumination means in an assembled state.

FIG. 8 shows a cross-section of the illumination means 80. The illumination means 80 is implemented as an annular segment. The wafer 6 passes through the remaining opening 82 (see FIG. 4). The board 100 is placed on the cooling body 90. The light sources 120 are arranged such that they are opposite a reflective element 103 formed in the metallic housing portion 101. From the reflective element 103, the light finally reaches the surface or the edge area of the wafer 6 through an optical element 105. The window 103 is formed for the passage of the light and may be provided with a diffusely scattering optical element. It is also possible that a diffusely scattering optical element is inserted in the window 105. A combination of a diffusely scattering optical element and a diffractive optical element for beam shaping is also contemplated. The reflective element 103 of the metallic housing portion 101 is an integral part of the housing portion 101. The reflective element 103 may be designed such that it is also suitable for beam shaping. The metallic housing portion 101 may be made as a rotary part. In a preferred embodiment, the metallic housing portion 101 is made of aluminum. The reflective element 103 is provided with a reflective coating. The reflective coating may be a metal coating and/or a dielectric coating. It is particularly advantageous if the dielectric coating has a filtering function for the light coming from the light sources.

The illumination means 80 for the illumination of the edge area of flat substrates is implemented as an annular segment. The edge area of the flat substrate 6 extends into the opening 82. A plurality of light sources 120 is arranged on a board 100 in the shape of an annular segment 81 in the housing. Inside the housing, a reflective element 103 is provided such that the light from the light sources 120 does not impinge perpendicularly on the upper edge area 6a, the lower edge area 6c and the front area 6b of the flat substrate 6.

The inspection means is equipped with the illumination means 80. The inspection means comprises several work stations 9, 10 and 12 and a changer 14 for the flat substrate. At least one of the work stations has an illumination means 80 associated therewith, which is implemented as an annular segment 81 and surrounds the edge area of the flat substrate 6. A plurality of light sources 120 is arranged on a board 100 also having the shape of an annular segment, in a housing. Inside the housing, a reflective element 103 is provided such that the light from the light sources 120 does not impinge perpendicularly on the upper edge area 6a, the lower edge area 6c and the front area 6b of the flat substrate 6.

The invention has been described with reference to a preferred embodiment. However, it is conceivable for someone skilled in the art that modifications or changes may be made to the invention without departing from the scope of the following claims.

What is claimed is:

1. An illumination means, comprising: a single annular segment defining an opening between ends of the single annular segment and the ends being operatively arranged for receiving an edge area of a wafer, the single annular segment including:
a plurality of light sources formed as light-emitting diodes arranged on the annular segment; a housing, wherein the plurality of light sources are arranged on a board inside the housing; and, a reflective element arranged inside the housing such that light emitted from the plurality of light sources does not impinge perpendicularly on an upper edge area, a lower edge area and a front area of the wafer, and wherein the plurality of light sources are arranged opposite the reflective element inside the housing; wherein the housing comprises: the single board shaped as the single annular segment; a cover arranged opposite the upper edge area, the lower edge area and the front area of the wafer, said cover in the shape of the single annular segment; and, a window arranged to allow the passage of the light from the light sources therethrough and wherein first and second lids are arranged to close the housing at respective end areas of the housing, each of said end areas being the ends of the single annular segment and the window includes a diffusely scattering optical element and/or a diffractive optical element for beam shaping; and, wherein a beam path of the light emitted by the plurality of light sources is parallel to the upper edge area and the lower edge area of said wafer when the wafer is received by the annular segment.

2. The illumination means recited in claim 1, wherein the board is divided into three segments, wherein each segment of the three segments are separately operatable, and the light-emitting diodes are arranged evenly on the board.

3. The illumination means recited in claim 2, wherein the board is mounted on a cooling body.

4. The illumination means as recited in claim 1, wherein the reflective element is formed as an integral part of the housing, the reflective element has a shape operatively arranged for beam-shaping, and the reflective element comprises a reflective coating.

5. The illumination means as recited in claim 4, wherein the reflective coating comprises a metal coating and/or a dielectric coating also having a filtering function for the light from the light sources.

6. The illumination means recited in claim 1, wherein the light from the plurality of light sources may be set to be monochromatic and/or polychromatic.

7. The illumination means as recited in claim 6, wherein the light-emitting diodes comprise different color LEDs.

8. The inspection means recited in claim 1, wherein a diffusely scattering optical element is provided in the window for the passage of the light from the light sources.

9. The inspection means recited in claim 1, wherein a diffractive optical element for beam shaping is provided in the window for the passage of the light from the light sources.

10. The inspection means recited in claim 1, wherein a diffusely scattering optical element and a diffractive optical element for beam shaping are provided in the window for the passage of the light from the light sources.

11. An inspection means comprising: at least one work station; a changer for supplying a wafer to the at least one work station; an illumination means associated with at least one work station, wherein the illumination means is formed as a annular segment defining an opening between ends of the single annular segment and surrounds at least an edge area of the wafer; a housing, wherein a plurality of light sources are arranged on a board inside the housing, wherein the board has a shape substantially resembling the singular annular segment; a first camera, a second camera and a third camera arranged on a common carrier, the common carrier movable in a radial direction with respect to the wafer; and, a reflective element being provided inside the housing, such that the light from the light sources does not impinge perpendicularly on an upper edge area, a lower edge area and a front area of the wafer, and wherein the plurality of light sources are arranged opposite the reflective element inside the housing; wherein the housing comprises: the board shaped as the single annular segment; a cover arranged opposite the upper edge area, the lower edge area and the front area of the wafer, the cover in the shape of the single annular segment; and, a window arranged to allow the passage of the light from the light sources therethrough, and wherein a lid is arranged to close the housing at each end area of the housing, each of the end areas being the ends of the single annular segment, and the window includes a diffusely scattering optical element and/or a diffractive optical element for beam shaping; and, wherein light from each of the plurality of light sources impinges on the wafer at respective angles with respect to the surface normal angle of the wafer and said light arrives at least on one of said first, second and third cameras at the same angle.

12. The inspection means recited in claim 11, wherein the plurality of light sources are formed by a plurality of light-emitting diodes arranged evenly on the board, and the board is partitioned into three separately operatable segments;
wherein the three separately operable segments are located on the board.

13. The inspection means recited in claim 12, wherein the board with the light-emitting diodes is mounted on a cooling body.

14. The inspection means recited in claim 11, wherein the reflective element is formed as an integral part of the housing, wherein the reflective element is provided with such a shape that it is usable for beam shaping.

15. The inspection means recited in claim 11, wherein the housing has a metallic housing portion, wherein the metallic housing portion comprises a rotary part made of aluminum, and wherein the reflective element comprises a reflective coating.

16. The inspection means recited in claim 15, wherein the reflective coating comprises a metal coating and/or a dielectric coating also having a filtering function for the light from the light sources.

17. The inspection means recited in claim 11, wherein the light from the plurality of light sources is polychromatic.

18. The inspection means recited in claim 11, wherein the light from the light sources is monochromatic.

19. The inspection means recited in claim 11, wherein the light from the light sources may be set to be monochromatic and/or polychromatic.

20. The inspection means recited in claim 17, wherein the plurality of light sources emits light of different colors.

21. The inspection means recited in claim 17, wherein the light sources are LEDs arranged on various segments, wherein each of the various segments carry LEDs of different color.

* * * * *